United States Patent [19]

Seki et al.

[11] Patent Number: 5,352,828
[45] Date of Patent: Oct. 4, 1994

[54] PROCESS FOR STABILIZING AQUEOUS ACRYLAMIDE SOLUTION

[75] Inventors: Susumu Seki; Akihisa Furuno, both of Kanagawa, Japan

[73] Assignee: Nitto Chemical Industry Co., Ltd., Tokyo, Japan

[21] Appl. No.: 885,358

[22] Filed: May 19, 1992

[30] Foreign Application Priority Data

May 22, 1991 [JP] Japan .................................. 3-145180

[51] Int. Cl.$^5$ .......................................... C07C 209/90
[52] U.S. Cl. .......................................... 564/4; 564/2; 564/204; 564/206; 435/129
[58] Field of Search ...................... 564/4, 2, 204, 206; 562/512; 435/129

[56] References Cited

U.S. PATENT DOCUMENTS

| 2,863,918 | 12/1958 | Bikales et al. | 564/4 |
| 2,927,942 | 3/1960 | Bikales et al. | 564/4 |
| 4,233,240 | 11/1980 | Linke et al. | 564/4 |

FOREIGN PATENT DOCUMENTS

| 1030826 | 5/1958 | Fed. Rep. of Germany . | |
| 1252199 | 10/1967 | Fed. Rep. of Germany | 564/4 |
| 1402695 | 5/1965 | France . | |
| 39-10109 | 6/1964 | Japan . | |
| 39-23548 | 10/1964 | Japan . | |
| 40-7171 | 4/1965 | Japan . | |
| 40-7172 | 4/1965 | Japan . | |
| 41-1773 | 2/1966 | Japan . | |
| 45-11284 | 4/1970 | Japan . | |
| 47-4043 | 2/1972 | Japan . | |
| 47-28766 | 7/1972 | Japan . | |
| 48-3818 | 2/1973 | Japan . | |
| 46711 | 4/1979 | Japan | 564/2 |
| 01047750 | 2/1989 | Japan | 564/4 |
| 2270846A | 11/1990 | Japan | 564/4 |

OTHER PUBLICATIONS

Database WPI Week 7232, Derwent Publications Ltd., London, GB; AN 72-51015T [32] for JP-B-47-28766 (Mitsubishi Chemical Inds) Mar. 12, 1969.

*Primary Examiner*—Shailendra Kumar
*Attorney, Agent, or Firm*—Sughrue, Mion, Zinn, Macpeak & Seas

[57] ABSTRACT

A process for the stabilization of an aqueous acrylamide solution is described which includes adding at least one compound selected from water-soluble monocarboxylic acid salts having at least two carbon atoms to an aqueous solution of acrylamide in an amount of from 20 to 5,000 ppm as acid per acrylamide. According to the present invention, a high purity aqueous acrylamide solution which is markedly stable, even under an iron surface-contacting condition, without causing problems such as the polymerization of acrylamide can be provided by adding a water-soluble monocarboxylic acid salt having at least two carbon atoms.

6 Claims, No Drawings

PROCESS FOR STABILIZING AQUEOUS ACRYLAMIDE SOLUTION

FIELD OF THE INVENTION

This invention relates to a process for the stabilization of an aqueous acrylamide solution. Acrylamide is an exceedingly useful substance as a starting material for polymers which can be used as a coagulating agent, a thickener, a petroleum recovering agent, a paper strength fortifier, a thickening agent for paper-making, and the like.

BACKGROUND OF THE INVENTION

A sulfuric acid hydrolysis process in which acrylamide sulfate is obtained by heating acrylonitrile in the presence of sulfuric acid and water was used initially as an industrial process for the production of acrylamide. This process, however, has been replaced by a copper, catalyst process in which acrylamide is obtained by direct hydration of acrylonitrile in the presence of a copper catalyst such as copper metal, reduced copper, Raney copper, or the like. In addition, a microbiological method in which a microbial nitrile-hydration enzyme (nitrile hydratase) is used has recently been developed and put into practical use as an industrial process for the production of high purity acrylamide.

Of these acrylamide production processes, the copper catalyst process is apt to cause side reactions because of the generally high reaction temperature (60° to 150° C.) and reaction pressure (0 to 20 kg/cm$^2$), thus requiring a refining step for the removal of by-products and other incidental impurities such as catalyst-originated metal ions. In the case of the microbiological method, on the other hand, there are no impurities such as metal ions as a matter of course, and the amount of by-products is markedly small in comparison with the copper catalyst process, because the enzyme reaction is effected under ordinary temperature and pressure, thus rendering possible simplification of a refining step or even its omission. However, when a high performance polymer is produced for use in the aforementioned coagulating agent and the like, it is necessary to increase the purity of acrylamide as much as possible.

However, as in the case of many other unsaturated monomers, acrylamide is apt to cause polymerization not only by its exposure to light or heat but also by its contact with an iron surface, and such properties cannot be altered by improving purity of its aqueous solution.

Because of its unstable nature, acrylamide is usually kept at a low temperature (about 20° C.) in the dark, avoiding contact with an iron surface, in addition to the use of a stabilizing agent therewith.

A number of stabilizing agents have been proposed for this purpose, including, for example: 8-hydroxyquinoline and cupferron iron salt (JP-B-39-23548); thiourea, ammonium thiocyanate and nitrobenzene (JP-B-39-10109); ferron (JP-B-40-7171); furildioxime (JP-B-40-7172); a chrome-cyanogen complex (JP-B-41-1773); p-nitrosodiphenylhydroxylamine (JP-B-45-11284); 2,6-di-t-butyl-3-dimethylamino-4-methylphenol (JP-B-47-4043); 4-aminoantipyrine, oxalic acid and hydroxylamine sulfate (JP-B-47-28766); and a mixture of manganese with a chelate compound (JP-B-48-3818). (The term "JP-B" as used herein means an "examined Japanese patent publication")

These stabilizing agents are used in the acrylamide production process for the purpose of preventing polymerization, stabilizing precipitated crystals, and stabilizing an aqueous acrylamide solution. These agents are classified as polymerization inhibitors or polymerization retarders. As a consequence, when compounds among these stabilizing agents have a low polymerization retarding ability, they must be used in a considerably large amount, which is not economical, while those having a high retarding capacity will exert an adverse influence on polymerization, even in a small amount. In addition, these stabilizing agents are not always effective when used to stabilize an aqueous acrylamide solution which is in contact with an iron surface. In actuality, it is almost impossible to protect acrylamide perfectly from contact with an iron surface during its production, purification and storage steps, for example, from its local contact with an iron surface caused by a pin hole or peeling of a vessel lining, exposure of a weld zone of piping, or the like.

SUMMARY OF THE INVENTION

The present inventors have conducted intensive studies on the stability of high purity aqueous acrylamide solutions under iron surface-contacting conditions, and, as a result, found that the addition of a water-soluble monocarboxylic acid salt having at least two carbon atoms was markedly effective for the stabilization of the aqueous solution, which cannot be expected from the teachings of the prior art. The present invention has been accomplished on the basis of this finding.

Particularly, the present invention provides a process for the stabilization of an aqueous acrylamide solution which comprises adding at least one compound selected from water-soluble monocarboxylic acid salts having at least two carbon atoms to an aqueous solution of acrylamide in an amount of from 20 to 5,000 ppm as acid per acrylamide.

DETAILED DESCRIPTION OF THE INVENTION

Aqueous acrylamide solution

The aqueous acrylamide solution to be used in the process of the present invention may be an aqueous acrylamide solution produced by the sulfuric acid hydration process, the copper catalyst process, or the recently industrialized microbiological method. Preferably, it is a high purity aqueous acrylamide solution which contains substantially no metal corrosion-enhancing ions such as sulfate ions (about 3 ppm or less per acrylamide) from a starting material, a catalyst and the like.

Examples of the microbiological method for the production of acrylamide from acrylonitrile are disclosed, for example, in JP-B-56-17918 (corresponding to U.S. Pat. No. 4,248,968), JP-B-59-37951 (corresponding to U.S. Pat. No. 4,637,982) and JP-A-2-470 (corresponding to EP-A-0307926) (the term "JP-A" as used herein means an "unexamined published Japanese patent application"). The methods described in these reference are a method that utilizes a nitrile hydratase obtained by microorganisms belonging to genus Corynebacterium or Nocardia, a method that utilizes a nitrile hydratase obtained by microorganisms belonging to genus Pseudomonas and a method that utilizes a nitrile hydratase obtained by microorganisms of *Rhodococcus rhodochrous*, respectively.

Monocarboxylic acid salt

The monocarboxylic acid salt to be used in the process of the present invention may be a salt of either a saturated or an unsaturated water-soluble monocarboxylic acid having at least two carbon atoms. Illustrative examples of the saturated monocarboxylic acids include acetic acid, propionic acid, n-capronic acid, and the like. Butyric acid and the like having a strong odor are not preferred from the viewpoint of working atmosphere in the manufacturing process and the handling of product. Illustrative examples of unsaturated monocarboxylic acids include acrylic acid, methacrylic acid, vinylacetic acid, and the like. Typical examples of salts include sodium salt, potassium salt, ammonium salt, and the like. The monocarboxylic acid may be added not only in the salt form but also in the acid form, provided that a salt is formed in the aqueous acrylamide solution. The pH value is controlled generally within the range of from about 6 to about 8.

The monocarboxylic acid salt is used in an amount of from 20 to 5,000 ppm, preferably from 50 to 1,000 ppm, as acid per acrylamide. Amounts of the monocarboxylic acid smaller than 20 ppm would bear no significant stabilization effect, amounts of the monocarboxylic acid larger than 1,000 ppm would produce no proportionally greater effect, and amounts of the monocarboxylic acid larger than 5,000 ppm would spoil the purity of the aqueous acrylamide solution.

When used within the above 20 to 5,000 ppm range, the monocarboxylic acid salt of the present invention hardly exerts an influence on the polymerization reaction at the time of the production of an acrylamide polymer.

The present invention will now be illustrated in greater detail by way of the following examples, but it should be understood that the present invention is not deemed to be limited thereto. All parts, percents, ratios, and the like are by weight unless otherwise indicated.

EXAMPLE 1

A 50 ml capacity plastic container was charged with 30 g of a 50% by weight aqueous solution of recrystallized acrylamide (Note 1), a piece of doughnut-shaped iron (Note 2), and each of the stabilizing agents (Note 3) shown in Table 1. The container was then sealed and subjected to an accelerated stability test at 50° C. for 20 hours, or further at 70° C. for 70 hours when a sample showed enough stability at 50° C. for 20 hours. As a control, a sample with no stabilizing agent was treated in the same manner. The results are shown in Table 1.

Note 1: Acrylamide-HG for electrophoresis use (purity, 99%; Wako Pure Chemical Industries, Ltd.) was used without further treatment as the recrystallized acrylamide.

Note 2: A doughnut-shaped iron piece (outer diameter, 14 mm; inner diameter, 6 mm; thickness, 1 mm) was soaked in a 5 to 10% aqueous solution of hydrochloric acid for 15 minutes, washed with water, soaked in 1N sodium hydroxide for 1 minute, and then washed thoroughly with water. The thus treated iron piece was washed with acetone, air-dried, and then stored in a desiccator until its use.

Note 3: Each of the monocarboxylic acids was adjusted to pH 6 with sodium hydroxide prior to its addition to the aqueous acrylamide solution.

In the following table, the amount of each stabilizing agent added is expressed based on the acid component of the stabilizing agent.

TABLE 1

| Stabilizing Agent | Addition Amount (ppm, per acrylamide) | Heating Temperature and Time | | |
|---|---|---|---|---|
| | | 50° C. | | 70° C. |
| | | 3 hrs | 20 hrs | 70 hrs |
| None | — | B | C | — |
| Acetic acid salt | 200 | A | A | A |
| Propionic acid salt | 200 | A | A | A |
| n-Capronic acid salt | 200 | A | A | A |
| Acrylic acid salt | 200 | A | A | A |
| Methacrylic acid salt | 200 | A | A | A |
| Vinylacetic acid salt | 200 | A | A | A |

(Note) Test results were expressed as A to C by the following grading: A, no corrosion of the iron piece with a clear solution; B, formation of a gel mass on the iron piece; and C, popcorn-like polymer formation as a whole.

EXAMPLE 2

An aqueous acrylamide solution was prepared by the microbiological method under the following conditions.

(1) Preparation of biological catalyst:

Rhodococcus rhodochrous strain J-1 (FERMBP-1478, which has been deposited under Budapest treaty) disclosed in JP-A-2-470 (corresponding to EP-A-0307926) was inoculated into the following medium and cultured at 30° C. for 72 hours. Cells thus obtained were collected, washed, and then immobilized in the usual way with polyacrylamide gel to be used as a biological catalyst.

| | |
|---|---|
| Glucose | 10 g/l |
| $K_2HPO_4$ | 0.5 g/l |
| $KH_2PO_4$ | 0.5 g/l |
| $MgSO_4.7H_2O$ | 0.5 g/l |
| Yeast extracts | 1.0 g/l |
| Peptone | 7.5 g/l |
| Urea | 7.5 g/l |
| $CoCl_2$ | 10 mg/l |

(2) Preparation of aqueous acrylamide solution:

The biological catalyst obtained above was suspended in 1/400M sodium sulfate, and acrylonitrile was added to the suspension with stirring at 5° C. (pH 7) to obtain an aqueous solution containing about 30% by weight of acrylamide. After completion of the reaction, the biological catalyst was removed, and the resulting solution was concentrated under a reduced pressure of 60 mmHg ($8 \times 10^3$ Pa) at a water bath temperature of 63° C. to obtain an aqueous solution of 50% by weight acrylamide. The thus obtained aqueous acrylamide solution was passed through a mixed-bed column prepared from Amberlite IR-118 and Amberlite IRA-68 (manufactured by the Rohm & Haas Co.) to obtain a deionized high purity aqueous acrylamide solution.

Using the thus obtained deionized 50 wt % aqueous acrylamide solution, an accelerated stability test was carried out in the same manner as in Example 1, with the results shown in Table 2.

TABLE 2

| Stabilizing Agent | Addition Amount (ppm, per acrylamide) | Heating Temperature and Time | | |
|---|---|---|---|---|
| | | 50° C. | | 70° C. |
| | | 3 hrs | 20 hrs | 70 hrs |
| None | — | C | D | — |
| | 20 | A | A | B |

TABLE 2-continued

| Stabilizing Agent | Addition Amount (ppm, per acrylamide) | Heating Temperature and Time | | |
|---|---|---|---|---|
| | | 50° C. | | 70° C. |
| | | 3 hrs | 20 hrs | 70 hrs |
| Acrylic acid salt | 50 | A | A | A |
| | 200 | A | A | A |
| | 1,000 | A | A | A |
| | 5,000 | A | A | A |

(Note) Test results were expressed as A to D by the following grading: A, no corrosion of the iron piece with a clear solution; B, partial formation of gel on the iron piece; C, formation of a gel mass on the iron piece; and D, popcorn-like polymer formation as a whole.

As is evident from the above results, when a high purity aqueous acrylamide solution is maintained at 50° C. in the presence of an iron piece without adding the stabilizing agent of the present invention, a polymer substance (gel) starts to form on the surface of the iron piece after about 3 hours of the heating, and the gel is turned into a popcorn-like polymer as a whole after about 20 hours. In contrast, when the high purity acrylamide aqueous solution is heated under the same condition in the presence of 20 to 5,000 ppm (per acrylamide) of a water-soluble monocarboxylic acid salt having at least two carbon atoms, the aqueous acrylamide solution can be maintained markedly stably with no corrosion of the iron piece. Such excellent effects of the stabilizing agent of the present invention hardly change, even when the aqueous acrylamide solution is maintained at 70° C. for 70 hours.

Thus, it is apparent that the present invention provides a process for the stabilization of an aqueous acrylamide solution.

According to the process of the present invention, a high purity aqueous acrylamide solution which is markedly stable, even under an iron surface-contacting condition, without causing problems such as the polymerization of acrylamide can be provided by adding at least one water-soluble monocarboxylic acid salt having at least two carbon atoms to the aqueous acrylamide solution in an amount of from 20 to 5,000 ppm as acid per acrylamide.

As a secondary feature of the present invention, the corrosion of an iron surface can be inhibited, which further improves the stability of the aqueous acrylamide solution. Since the monocarboxylic acid salt itself does not protect an iron surface from corrosion in an aqueous solution, such a stabilizing effect is a specific function which is exhibited only in an aqueous acrylamide solution.

While the invention has been described in detail and with reference to specific examples thereof, it will be apparent to one skilled in the art that various changes and modifications can be made therein without departing from the spirit and scope thereof.

What is claimed is:

1. A process for stabilizing an aqueous acrylamide solution, which comprises adding at least one compound selected from water-soluble monocarboxylic acid salts having at least two carbon atoms to an aqueous solution of acrylamide in an amount of from 20 to 5,000 ppm as acid per acrylamide.

2. A process for stabilizing an aqueous acrylamide solution as claimed in claim 1, wherein the amount of said at least one compound selected from water-soluble monocarboxylic acid salts having at least two carbon atoms is from 50 to 1,000 ppm as acid per acrylamide.

3. A process for stabilizing an aqueous acrylamide solution as claimed in claim 1, wherein the aqueous solution of acrylamide is a high purity aqueous acrylamide solution.

4. A process for stabilizing an aqueous acrylamide solution as claimed in claim 1, wherein the aqueous solution of acrylamide is produced by a microbiological method.

5. A process for stabilizing an aqueous acrylamide solution as claimed in claim 1, wherein the at least one compound selected from water-soluble monocarboxylic acid salts having at least two carbon atoms is formed from a monocarboxylic acid which does not have a strong odor.

6. A process for stabilizing an aqueous acrylamide solution as claimed in claim 1, wherein the monocarboxylic acid is selected from the group of acetic acid, propionic acid, n-capronic acid, acrylic acid, methacrylic acid and vinylacetic acid.

* * * * *